(12) United States Patent
Fein et al.

(10) Patent No.: US 9,333,261 B2
(45) Date of Patent: May 10, 2016

(54) COMBINATION THERAPY FOR SKIN DISORDERS

(71) Applicant: M. Alphabet 1, LLC, Deerfield Beach, FL (US)

(72) Inventors: Howard Fein, Rolling Hills Estates, CA (US); Mindy B. Berlin, Delray Beach, FL (US)

(73) Assignee: M. ALPHABET 1, LLC, Deerfield Beach, FL (US)

( * ) Notice: Subject to any disclaimer, the term of this patent is extended or adjusted under 35 U.S.C. 154(b) by 0 days.

(21) Appl. No.: 14/157,754

(22) Filed: Jan. 17, 2014

(65) Prior Publication Data

US 2014/0199375 A1 Jul. 17, 2014

Related U.S. Application Data

(62) Division of application No. 13/518,818, filed as application No. PCT/US2011/031886 on Apr. 11, 2011, now Pat. No. 8,653,129.

(60) Provisional application No. 61/349,240, filed on May 28, 2010, provisional application No. 61/369,391, filed on Jul. 30, 2010.

(51) Int. Cl.
| | |
|---|---|
| *A61K 45/06* | (2006.01) |
| *A61K 31/135* | (2006.01) |
| *A61K 31/353* | (2006.01) |
| *A61K 31/496* | (2006.01) |
| *A61K 31/565* | (2006.01) |
| *A61K 31/65* | (2006.01) |
| *A61K 9/00* | (2006.01) |
| *A61K 9/127* | (2006.01) |
| *A61K 9/48* | (2006.01) |
| *A61K 9/70* | (2006.01) |

(52) U.S. Cl.
CPC .............. *A61K 45/06* (2013.01); *A61K 9/0014* (2013.01); *A61K 9/0053* (2013.01); *A61K 9/127* (2013.01); *A61K 9/48* (2013.01); *A61K 9/7023* (2013.01); *A61K 31/353* (2013.01); *A61K 31/496* (2013.01); *A61K 31/565* (2013.01); *A61K 31/65* (2013.01); *A61K 31/135* (2013.01)

(58) Field of Classification Search
CPC . A61K 31/535; A61K 31/496; A61K 31/565; A61K 31/65; A61K 45/06; A61K 9/0014; A61K 9/0053; A61K 9/127; A61K 9/48; A61K 9/7023; A61K 31/135; A61K 31/353
See application file for complete search history.

(56) References Cited

U.S. PATENT DOCUMENTS

| | | | | |
|---|---|---|---|---|
| 4,925,833 | A  * | 5/1990 | McNamara et al. | .......... 514/152 |
| 2007/0225301 | A1 | 9/2007 | Weidner et al. | |
| 2008/0188446 | A1* | 8/2008 | Muldoon et al. | .............. 514/154 |
| 2010/0076071 | A1 | 3/2010 | Lephart et al. | |

FOREIGN PATENT DOCUMENTS

| | | |
|---|---|---|
| EP | 0114003 | 7/1984 |
| WO | WO 2004009035 A2 * | 1/2004 |
| WO | WO 2005/107770 A1 | 11/2005 |
| WO | WO 2010/038234 A1 | 4/2010 |

OTHER PUBLICATIONS

Remington: The Science and Practice of Pharmacy, 2005, Lippincott Williams and Wilkins, 21$^{st}$ ed., pp. 948-949.*
Blair et. al., The Journal of Nutrition, 2003, American Society for Nutritional Sciences, vol. 133, pp. 2262-2267.*
Skidmore et al., "Effects of Subantimicrobial-Dose Doxycyline in the Treatment of Moderate Acne," Arch. Dermatol. 139, pp. 459-464 (2003).
Brown et al., "The chemopreventive action of equol enantiomers in a chemically induced animal model of breast cancer," Carcinogenesis 31(5): 886-893 (2010).
Del Rosso and Kim, "Optimizing use of oral antibiotics in acne vulgaris," Dermatol.Clin. 27: 33-42 (2009).
Esterly et al., "The effect of antimicrobial agents on leukocyte chemotaxis," J. Invest. Dermatol. 70(1): 51-55 (1978).
Harrison, "A comparison of doxycycline and minocycline in the treatment of acne vulgaris," Clinical and Experimental Dermatology 13: 242-244 (1988).
Kircik, "Doxycycline and minocycline for the management of acne: a review of efficacy and safety with emphasis on clinical implications," Journal of Drugs in Dermatology, 9(11): 1407-1411 (2010).
Knutson, "Ultrastructural observations in acne vulgaris: the normal sebaceous follicle and acne lesions,"Journal of Investigative Dermatology 62: 288 (1974).
Leyden JJ, McGinley KJ, Mills OH, Kligman AM, "Propionibacterium levels in patients with and without acne vulgaris," J Invest Dermatol 65: 382-4 (1975).
Marples RR, Leyden JJ, Stewart RN, Mills OH, Jr., Kligman AM, "The skin microflora in acne vulgaris." J. Invest. Dermatol. 62: 37-41 (1974).
Muthyala et al., "Equol, a natural estrogenic metabolite from soy isoflavones: convenient preparation and resolution of R- and S-equols and their differing binding and biological activity through estrogen receptors alpha and beta," Bioorganic & Medicinal Chemistry 12:1559-1567 (2004).
Setchell et al., "S-Equol, a potent ligand for estrogen receptor β, is the exclusive enantiomeric form of the soy isoflavone metabolite produced by human intestinal bacterial flora," American Journal of Clinical Nutrition 81: 1072-1079 (2005).

(Continued)

*Primary Examiner* — Sarah Pihonak
(74) *Attorney, Agent, or Firm* — Duane Morris LLP

(57) ABSTRACT

The present invention provides a novel therapeutic combination comprising one or more anti-androgen agents and one or more antibiotic/anti-inflammatory agents or pharmaceutically acceptable salts or hydrates thereof, useful for the treatment of a dermatological disorder.

12 Claims, No Drawings

(56) References Cited

OTHER PUBLICATIONS

Setchell et al., "The pharmacokinetic behavior of the soy isoflavone metabolite S-(−)equol and its diastereoisomer R-(+)equol in healthy adults determined by using stable-isotope-labeled tracers," American Journal of Clinical Nutrition 90: 1029-1037 (2009).

Setchell and Clerici, "Equol: History, Chemistry, and Formation," The Journal of Nutrition 140(7) 1355S-1362S (2010).

Setchell and Clerici, "Equol: Pharmacokinetics and Biological Actions," The Journal of Nutrition 140(7) 1363S-1368S (2010).

Setchell and Cole, "Method of defining equol-producer status and its frequency among vegetarians," Journal of Nutrition 136(8): 2188-2193 (2006).

Shinkaruk et al., "Comparative effects of R- and S-equol and implication of transactivation functions (AF-1 and AF-2) in estrogen receptor-induced transcriptional activity," Nutrients 2: 340-354 (2010).

Smit, "Minocycline versus doxycycline in the treatment of acne vulgaris: a double-blind study," Dermatologica, 157: 186-190 (1978).

Tan, "Antibacterial therapy for acne: a guide to selection and use of systemic agents," American Journal of Clinical Dermatology 4(5): 307-314 (2003).

Thiboutot et al., "Activity of the type I 5α-reductase exhibits regional differences in isolated sebaceous glands and whole skin," Journal of Investigative Dermatology 105(2): 209-214 (1995).

Brown and Shalita, "Acne vulgaris," The Lancet 351:1871-1876 (1998).

Downing et al., "Essential fatty acids and acne," J. Am. Acad. Dermatol. 14:221-225 (1986).

Driscoll et al., "Long-term oral antibiotics for acne: is laboratory monitoring necessary?" J. Am. Acad. Dermatol. 28:595-602 (1993).

Eady, "Bacterial resistance in acne," Dermatology 196:59-66 (1998).

Esterly et al., "Neutrophil chemotaxis in patients with acne receiving oral tetracycline therapy," Arch. Dermatol. 120:1308-1313 (1984).

Feldman et al., "Diagnosis and treatment of acne," Am. Fam. Physician 69(9):2123-2130 (2004).

Freinkel et al., "Effect of tetracycline on the composition of sebum in acne vulgaris," N. Engl. J. Med. 273:850-854 (1965).

Haider and Shaw, "Treatment of acne vulgaris," JAMA 292(6):726-735 (2004).

Johnson, "Use of systemic agents in the treatment of acne vulgaris," Am. Fam. Physician 62(8):1823-1830 (2000).

Krakowski and Eichenfeld, "Pediatric acne: clinical presentations, evaluation, and management," J. Drugs Dermatol. 6(6):589-593 (2007).

Leyden, "Therapy for acne vulgaris," N. Engl. J. Med. 336:1156-62 (1997).

Meynadier and Alirezai, "Systemic antibiotics for acne," Dermatology 196:135-139 (1998).

Miller et al., "A practical approach to antibiotic treatment in women taking oral contraceptives," J. Am. Acad. Dermatol. 30:1008-11 (1994).

Parish et al., "The treatment of acne vulgaris with low dosage doxycycline," Acta. Dermatovenerol. Croat. 13(3):156-159 (2005).

Plewig et al., "Double-blind study of doxycycline in acne vulgaris," Arch. Dermatol. 101(4):435-438 (1970).

Rothman and Lucky, "Acne vulgaris," Adv. Dermatol. 8:347-374 (1993).

Sapardin and Fleischmajer, "Tetracyclines: nonantibiotic properties and their clinical implications," JAAD 54(2):258-265 (2006).

Smith et al., "Safety of doxycycline and minocycline: a systematic review," Clin. Ther. 27(9):1329-1342 (2005).

Thiboutot et al., "Activity of the type I 5α-reductase is greater in the follicular infrainfundibulum compared with the epidermis," British Journal of Dermatology 136:166-171 (1997).

Tsankov, "Tetracyclines in dermatology," Clinics in Dermatology 21:33-39 (2003).

Wang et al., "Susceptibility of propionibacterium acnes to seventeen antibiotics," Antimicrob. Agents Chemother. 11(1):171-173 (1977).

Webster, "Acne," Curr. Probl. Dermatol. 8:237-268 (1996).

Del Rosso, "Recently approved systemic therapies for acne vulgaris and rosacea," Cutis, 80:113-120 (2007).

Goulden et al., "Post-adolescent acne: a review of clinical features," Br. J. Dermatol., 136:66-70 (1997).

Goulden et al., "Prevalence of facial acne in adults," J. Am. Acad. Dermatol., 41:577-580 (1999).

Holland and Anthony, "The role of inflammation in the pathogenesis of acne and acne scarring," Semin. Sutan. Med. Surg., 24:79-83 (2005).

Leyden et al., "Clinical considerations in the treatment of acne vulgaris and other inflammatory skin disorders: focus on antibiotic resistance," Cutis, 79(suppl 6): pp. 9-25 (2007).

Powell and Beveridge, "Sebum excretion and sebum composition in adolescent men with and without acne vulgaris," Br. J. Derm., 82:243-249 (1970).

Reboli and Del Bene, "Oral antibiotic therapy of dermatologic conditions" Dermatologic Clinics, 6(4):497-520 (1988).

Shapiro et al., "Comparative safety of tetracycline, minocycline, and doxycycline," Arch. Dermatol., 133:1224-1230 (1997).

Sloan and Scheinfeld, "The use and safety of doxycycline hyclate and other second-generation tetracyclines," Expert Opin. Drug Safety, 7(5): 571-577 (2008).

Song et al., "Antibiotic susceptibility of *Propionibacterium acnes* isolated from acne vulgaris in Korea," J. Dermatol., 38:667-673 (2011).

Stewart et al., "Sebaceous gland activity and serum dehydroepiandrosterone sulfate levels in boys and girls," Arch. Dermatol., 128:1345-1348 (1992).

Tan et al., "Antibiotic sensitivity of *Propionibacterium acnes* isolates studied in a skin clinic in Singapore," Arch. Dermatol., 135:723 (1999).

Tan and Tan, "Acne vulgaris: a review of antibiotic therapy," Expert Opin. Pharmacother., 6(3):409-418 (2005).

The North American Menopause Society, "NAMS 2011 isoflavones report: the role of soy isoflavones in menopausal health: report of the North American Menopause Society/Wulf H. Utian Translational Science Symposium in Chicago, IL (Oct. 2010)" Menopause: The Journal of the North American Menopause Society, 18(7):732-753 (2011).

Van Vlem et al., "Immunomodulating effects on antibiotics: literature review," Infection, 24(4):275-291 (1996).

White, "Recent findings in the epidemiologic evidence, classification and subtypes of acne vulgaris," J. Am. Acad. Dermatol., 39:S34-S37 (1998).

Supplementary European search report, Feb. 21, 2014.

European search opinion, Feb. 21, 2014.

Ochsendorf, F., "Systemic antibiotic therapy of acne vulgaris" JDDG: Journal der Deutschen Dermatologischen Gesellschaft, vol. 4, pp. 828-841, 2006.

Bu et. al., "Influences of dietary soy isoflavones on metabolism but not nociception and stress hormone responses in ovariectomized female rats," Reproductive Biology and Endocrinology, 3:1-8, 2005.

Tanaka et. al., "Antibacterial activity of isoflavonoids isolated from Erythrina variegata against methicillin-resistant *Staphylococcus aureus*," Letters in Applied Microbiology, 35;494-498, 2002.

Webster, "Acne vulgaris," British Medical Journal, 325:475-479, 2002.

Yang et. al., "Three New Phenolic Compounds from a Manipulated Plant Cell Culture, Mirabilis Jalapa," Journal of Natural Products, 64:313-317, 2001.

"Hormonal Therapy of Acne," Indian Journal of Dermatology, Venereology, & Leprology, 75, supplement 1:S44-S46, 2009.

* cited by examiner

COMBINATION THERAPY FOR SKIN DISORDERS

CROSS-REFERENCE TO RELATED APPLICATIONS

This application is a divisional application of U.S. application Ser. No. 13/518,818, filed Jun. 22, 2012, which is a U.S. national phase application filed under 35 U.S.C. §371 of International Application No. PCT/US2011/031886, which was filed Apr. 11, 2011, which claims the benefit of the filing dates of U.S. Provisional Application Nos. 61/349,240, filed May 28, 2010 and 61/369,391, filed Jul. 30, 2010. The content of these earlier filed applications is hereby incorporated by reference in the present application in its entirety.

FIELD OF THE INVENTION

The present invention is directed to a therapy comprising a novel combination of one or more anti-androgen agents and one or more antibiotic/anti-inflammatory agents or pharmaceutically acceptable salts or hydrates thereof, useful for the treatment of a dermatological disorder such as acne.

BACKGROUND OF THE INVENTION

Acne is a disorder of the pilosebaceous glands located on the face, chest and back. It is an almost universal disease, occurring in all races, predominantly among adolescents. The pathogenesis of acne is multi-factorial involving increased sebum production by the sebaceous glands, such as caused by increased activity of sebocytes, sometimes via peroxisome proliferator-activated receptor ligands; ductal hypercornification of the pilosebaceous unit of the dermis and epidermis and hyperkeratinization (increased activity of keratinocytes); inflammation; and the presence of the anaerobic bacteria *Propionibacterium acnes* (*P. acnes*).

The American Academy of Dermatology has reported that 85% to 100% of those aged 12-24 are affected by either intermittent or persistent acne, which in a number of adolescents results in scarring attributed to acne (Bershad, *The Mount Sinai Journal of Medicine*, Vol. 68, p. 279-286, 2001; White, *Journal of American Academy of Dermatology*, Vol. 39, p. S34-37, 1998). Furthermore, acne can remain problematic into the third to fifth decades of life, particularly in women. Tan et al., (*Journal of American Academy of Dermatology*, Vol. 44 (Supplement 3), p. 439-445, 2001), has reported that approximately 3% of all male adults and 12% of all female adults in the U.S. suffer from acne.

There is no cure for acne. Many medications are available for treating acne including topical retinoids (i.e., adapalene, tazarotene, tretinoin), antimicrobial and antibacterial agents (i.e., benzoyl peroxide, clindamycin, erythromycin, sodium sulfacetamide with or without sulfur), oral antibiotics (i.e., doxycycline, minocycline, tetracycline, azithromycin, trimethoprim-sulfamethoxazole (TMP/SMX), that primarily reduces the population of *P. acnes*, hormonal agents as anti-androgens (i.e., oral contraceptives) that decrease sebum secretion, systemic retinoids (i.e., isotretinoin), and topical aminolevulinic acid plus blue light (also known as photodynamic theory).

Various agents administered in acne treatments exhibit direct or indirect antibiotic activity but also directly suppress inflammation by decreasing neutrophil chemotaxis and down-regulate the expression of pro-inflammatory mediators. Oral antibiotics are indicated for several groups of patients with inflammatory acne. They include tetracyclines (i.e., tetracycline, doxycycline, minocycline, erythromycin, clindamycin, and cotrimoxazole).

With the high incidence of acne and other dermatological disorders that are of a major clinical health concern to both males and females, new innovative approaches are urgently needed at both the basic science and clinical levels to decrease the incidence of dermatological disorders.

SUMMARY OF THE INVENTION

The present invention provides a novel pharmaceutical composition comprising one or more anti-androgen agents and one or more antibiotic/anti-inflammatory agents or pharmaceutically acceptable salts or hydrates thereof, useful for the treatment of a dermatological disorder such as acne. The therapy combination of the present invention provides a synergistic effect in treating a subject with a dermatological disorder.

The present invention also provides a method for treating or preventing a dermatological disorder by administering a pharmaceutical composition comprising one or more anti-androgen agents and one or more antibiotic/anti-inflammatory agents or pharmaceutically acceptable salts or hydrates thereof.

DETAILED DESCRIPTION OF THE INVENTION

This invention provides novel pharmaceutical compositions comprising one or more anti-androgen agents and one or more antibiotic/anti-inflammatory agents as a combination of separate active agents or as a combined composition comprising both active agents. Such compositions are useful for suppressing, inhibiting, preventing, alleviating or treating a dermatological disorder, including, but not limited to, acne vulgaris, telogen effluvium, androgenetic alopecia, and acne rosacea.

The combination of the present invention can be administered at any time and in any effective form. The anti-androgen agent and the antibiotic/anti-inflammatory agent may be administered simultaneously, e.g., as a single combination or dosage unit (e.g., a pill or liquid containing both compositions), or they may be administered as separate compositions, but at the same time (e.g., where one drug is administered intravenously and the other is administered orally or intramuscularly). The anti-androgen agent and the antibiotic/anti-inflammatory agent may also be administered sequentially at different times.

It is understood that the anti-androgen agents and antibiotic/anti-inflammatory agents of the present invention include all analogs, isomers, metabolites, derivatives, pharmaceutically acceptable salts, N-oxides, hydrates or any combination thereof.

Anti-Androgen Agents:

Examples of general anti-androgen agents used singly or in combination in the present invention are, but not limited to, oral contraceptives, estrogen analogs, progesterone analogs, spironolactone, inocoterone acetate, cyproterone acetate, flutamide, nilutamide, bicalutamide, ketoconazole, finasteride, dutasteride, bexlosteride, izonsteride, epresteride, turosteride, an isoflavanoid, RU-58642, RU-56279, WS9761 A and B, RU-59063, RU-58841, bexlosteride, LG-2293, L-245976, LG-121071, LG-121091, LG-121104, LGD-2226, LGD-2941, YM-92088, YM-175735, LGD-1331, LGD-3303, BMS-357597, S-40503, BMS-482404, EM-4283, EM-4977, BMS-564929, BMS-391197, BMS-434588, BMS-487745, BMS-501949, SA-766, YM-92088, YM-580, LG-123303, LG-123129, PMCol, YM-175735, BMS-591305, BMS-591309, BMS-665139, BMS-665539, CE 590, 116BG33, 154BG31, arcarine, ACP-105, flutamide, hydroxyflutamide, bicalutamide, nilutamide, hydroxysteroid dehydrogenase inhibitors, PPARα ligands such as bezafibrate, fenofibrate, gemfibrozil; PPARγ ligands such as darglitazone, pioglitazone, rosiglitazone, isaglitazone, rivoglitazone, netoglitazone; dual acting PPAR ligands, such as naveglitazar, farglitazar, tesaglitazar, ragaglitazar, oxeglitazar, PN-2034, PPAR δ; 17-ketoreductase inhibitors, 3β-DHΔ4,6-isomerase inhibitors, 3β-DHΔ4,5-isomerase inhibitors, 17,20 desmolase inhibitors, p450c17 inhibitors, p450ssc inhibitors, and 17,20-lyase inhibitors, or mixtures thereof. The most preferred anti-androgen agents used in the present invention are spironolactone and an isoflavanoid.

Isoflavanoids (as illustrated below by the left-hand structure) or isoflavonoids (as illustrated below by the right-hand structure) that may be used in the present invention may have any of the following chemical formulae:

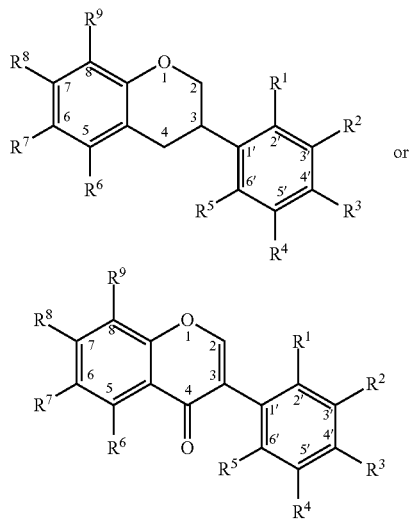

wherein $R^1$-$R^9$ may independently be H, OH, $C_{1-10}$ alkyl, $C_{1-10}$ alkenyl, $C_{1-10}$ alkynyl, vinyl, $N_3$, CN, Cl, Br, F, I, $NO_2$, C(O)O($C_{1-10}$ alkyl), C(O)O($C_{1-10}$ alkyl), C(O)O($C_{1-10}$ alkynyl), C(O)O($C_{1-10}$ alkenyl), O($C_{1-18}$ acyl), O($C_{1-10}$ alkyl), O($C_{1-10}$ alkenyl), S($C_{1-18}$ acyl), S($C_{1-10}$ alkyl), S($C_{1-10}$ alkynyl), S($C_{1-10}$ alkenyl), SO($C_{1-18}$ acyl), SO($C_{1-10}$ alkyl), SO($C_{1-10}$ alkynyl), SO($C_{1-10}$ alkenyl), $SO_2$($C_{1-18}$ acyl), $SO_2$($C_{1-10}$ alkyl), $SO_2$($C_{1-10}$ alkynyl), $SO_2$($C_{1-10}$ alkenyl), $O_3S$($C_{1-18}$ acyl), $O_3S$($C_{1-10}$ alkyl), $O_3S$($C_{1-10}$ alkenyl), $NH_2$, NH($C_{1-10}$ alkyl), NH($C_{1-10}$ alkenyl), NH($C_{1-10}$ alkynyl), NH($C_{1-18}$ acyl), N($C_{1-10}$ alkyl)$_2$, N($C_{1-18}$ acyl)$_2$, wherein alkyl, alkynyl, alkenyl and vinyl are optionally substituted by $N_3$, CN, one to three halogen (Cl, Br, F, I), $NO_2$, C(O)O($C_{1-10}$ alkyl), C(O)O($C_{1-10}$ alkyl), C(O)O($C_{1-10}$ alkynyl), C(O)O ($C_{1-10}$ alkenyl), O($C_{1-18}$ acyl), O($C_{1-10}$ alkyl), O($C_{1-10}$ alkenyl), S($C_{1-18}$ acyl), S($C_{1-10}$ alkyl), S($C_{1-10}$ alkynyl), S($C_{1-10}$ alkenyl), SO($C_{1-18}$ acyl), SO($C_{1-10}$ alkyl), SO($C_{1-10}$ alkynyl), SO($C_{1-10}$ alkenyl), $SO_2$($C_{1-18}$ acyl), $SO_2$($C_{1-10}$ alkyl), $SO_2$ ($C_{1-10}$ alkynyl), $SO_2$($C_{1-10}$ alkenyl), $O_3S$($C_{1-18}$ acyl), $O_3S$ ($C_{1-10}$ alkyl), $O_3S$($C_{1-10}$ alkenyl), $NH_2$, NH($C_{1-10}$ alkyl), NH($C_{1-10}$ alkenyl), NH($C_{1-10}$ alkynyl), NH($C_{1-18}$ acyl), N($C_{1-10}$ alkyl)$_2$, and N($C_{1-18}$ acyl)$_2$.

One such isoflavanoid is equol. Equol (4',7-isoflavandiol) is an isoflavandiol metabolized from daidzein, a type of isoflavone, by bacterial flora in the intestines. It is also produced commercially. While endogenous estrogenic hormones such as estradiol are steroids, equol is a nonsteroidal estrogen. In the current invention, the "S-" form is preferred. S-Equol preferentially activates estrogen receptor type β. S-Equol has the structure:

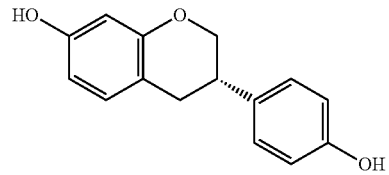 [SMILES: Oc1ccc([C@H]2COc3cc(O)ccc3C2)cc1]

It is appreciated that compounds of the present invention may have chiral centers and may exist in and be isolated in optically active and racemic forms. Some compounds may exhibit polymorphism. It is to be understood that the present invention encompasses any racemic, optically active, diastereomeric, polymorphic, tautomeric, or stereoisomeric form, or mixtures thereof, of a compound of the invention, which possess the useful properties described herein. It being well known in the art how to prepare optically active forms (for example, by resolution of the racemic form by recrystallization techniques, by synthesis from optically active starting materials, by chiral synthesis, or by chromatographic separation using a chiral stationary phase).

Antibiotic/Anti-Inflammatory Agents:

Examples of general antibiotic or anti-inflammatory agents used singly or in combination in the present invention are, but are not limited to, mupirocin, neomycin sulfate bacitracin, polymyxin B, 1-ofloxacin, clindamycin phosphate, gentamicin sulfate, metronidazole, hexylresorcinol, methylbenzethonium chloride, phenol, quaternary ammonium compounds, tea tree oil, steroidal agents such as corticosteroids such as hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene, (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, non-steroidal agents such as COX inhibitors, LOX inhibitors, p38 kinase inhibitors, immunosuppressant agents such as cyclosporin and cytokine synthesis inhibitors, tetracycline, minocycline, and doxycycline, or any combination thereof. The most preferred antibiotic agents are tetracycline, minocycline, and doxycycline.

Dermatological Disorder:

Examples of general dermatological disorders that are suppressed, inhibited, prevented, alleviated or treated in the present invention are, but are not limited to, dermatological pain, dermatological inflammation, acne, acne vulgaris, inflammatory acne, non-inflammatory acne, acne fulminans, nodular papulopustular acne, acne conglobata, acne rosacea, rosacea, acne excoriee, acne associated with endocrine disorders such as polycystic ovarian syndrome (PCOS) or Stein-Leventhal syndrome, dermatitis, bacterial skin infections, fungal skin infections, viral skin infections, parasitic skin infections, skin neoplasia, skin neoplasms, pruritus, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiform, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, purpura, moniliasis, candidiasis, baldness, androgenetic alopecia, Behcet's syndrome, cholesteatoma, Dercum disease, ectodermal dysplasia, gustatory sweating, nail patella syndrome, lupus, hives, telogen effluvium, Hailey-Hailey disease, chemical or thermal skin burns, scleroderma, aging skin, wrinkles, sun spots, necrotizing fasciitis, necrotizing myositis, gangrene, scarring, and vitiligo. The preferred dermatological disorders treated with the composition of the present invention are acne vulgaris, telogen effluvium, androgenetic alopecia, and acne rosacea.

Administration:

The pharmaceutical composition of the present invention may be administered in any form by any effective route, including, e.g., oral, parenteral, enteral, intravenous, suppository, intraperitoneal, topical, transdermal (e.g., using any standard patch), ophthalmic, nasally, local, non-oral, such as aerosol, inhalation, subcutaneous, intramuscular, buccal, sublingual, rectal, vaginal, intra-arterial, and intrathecal, etc. They can be administered alone, or in combination with any ingredient(s), active or inactive. The preferred route of administration is oral.

The pharmaceutical composition may be administered as a solid dosage form such as a tablet, capsule, pill, granule, pellet, powder, and the like. The solid dosage form of the present invention may comprise a coating that is resistant to gastric juices and dissolves as a function of the pH value of the release environment. By means of this coating, it is possible to ensure that the dosage form according to the present invention is delivered to its intended target. The crush resistant coating, which is resistant to gastric juices, may dissolve at a pH value of between 1 and 14

The solid dosage form of the present invention may exhibit crush resistance to mechanical strength over a wide temperature range of, for example, −25° C. to 40° C. The crush resistance may make the present invention virtually impossible to comminute or pulverise by chewing, grinding in a mortar, pounding, or any other means. As a consequence of the resistance to crushing, sustained release is maintained and an overdose due to improper handling of the dosage form is effectively prevented.

The pharmaceutical composition may also be administered as a liquid dosage form such as solutions, suspensions, dispersions, emulsions, foams, gels, oils, and the like.

The pharmaceutical composition of this invention may be administered by intravenous, intraarterial, or intramuscular injection of a liquid preparation. Suitable liquid formulations include solutions, suspensions, dispersions, emulsions, oils and the like.

The pharmaceutical composition may be administered topically to body surfaces, and is thus formulated in a form suitable for topical administration. Suitable topical formulations include liposomal beads, gels, ointments, creams, lotions, drops and the like. For topical administration, the anti-androgen agent and the antibiotic/anti-inflammatory agent are prepared and applied as solutions, suspensions, or emulsions in a physiologically acceptable diluent with or without a pharmaceutical carrier. For topical application, admixture of the compounds with conventional creams, lotions, or delayed release patches is acceptable. Such a cream or lotion may comprise any agent described herein, and, may be used to treat a dermatological disorder.

The liposomal beads that may be used in the present invention may control and increase concentration of the anti-androgen agent and the antibiotic/anti-inflammatory agent released at or near the desired target site of administration, thus enabling the user to control the locus and levels of the anti-androgen agent and the antibiotic/anti-inflammatory agent where it is most needed.

The benefit of having the anti-androgen agent and the antibiotic/anti-inflammatory agent in bead form is that they are not in direct contact with other active or inert suspensions including other liposomes. This includes second and third levels of bead formation and levels of hardening encapsulation.

The pharmaceutical composition may be administered as a suppository, for example a rectal suppository or a urethral suppository. Further, the pharmaceutical composition is administered by subcutaneous implantation of a pellet. The pellet may provide controlled release of a compound as herein described over a period of time.

The pharmaceutical composition of the present invention is primarily for administration to a host, which may comprise mammals, and particularly humans. It is expected that the physician will determine the actual dosage and duration of treatment, which will be most suitable for an individual and can vary with the age, weight and response of the particular individual.

Formulations:

The final pharmaceutical composition of the present invention may comprise from about 5 mg to about 2000 mg of an anti-androgen agent, from about 0.01 mg to about 5000 mg of an isoflavanoid, and from about 5 mg to about 2000 mg of an antibiotic/anti-inflammatory agent.

The preferred pharmaceutical composition of the present invention may comprise from about 25 mg to about 200 mg of an anti-androgen agent, from about 0.1 mg to about 500 mg of an isoflavanoid, and from about 50 mg to about 200 mg of an antibiotic/anti-inflammatory agent.

The pharmaceutical composition may be formulated with, but not limited to, pharmaceutically acceptable carriers or diluents, fillers, polymers, glidants, and lubricants.

Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, and polyvinyl pyrrolidone. The carrier may also comprise any of the substances described in Remington: The Science and Practice of Pharmacy (Gennaro and Gennaro, Eds, 20th edition, Lippincott Williams & Wilkins, 2000); Theory and Practice of Industrial Pharmacy ((Lachman et al., eds., 3rd edition, Lippincott Williams & Wilkins, 1986); Encyclopedia of Pharmaceutical Technology (Swarbrick and Boylan, eds., 2nd edition, Marcel Dekker, 2002).

The fillers can be chosen from, but are not limited to, powdered cellulose, sorbitol, mannitol, various types of lactose, phosphates and the like.

The polymers can be chosen from, but not limited to, hydrophilic or hydrophobic polymers such as derivatives of cellulose (for example methylcellulose, hydroxypropyl cellulose, hypromellose, ethylcellulose); polyvinylpirolidone (for example povidone, crospovidone, copovidone); polymethacrylates (for example Eudragit RS, RL); lypophillic components (for example glyceryl monostearate, glyceryl behenate); and various other substances such as for example hydroxypropyl starch, polyethylene oxide, carrageenan and the like. Most commonly, hydrophilic swelling polymers of suitable viscosity such as hypromellose are used, preferably in amounts above 5%, and more preferably above 8%.

Glidants can be chosen from, but not limited to, colloidal silicon dioxide, talc, magnesium stearate, calcium stearate, aluminium stearate, palmitic acid, stearic acid, stearol, cetanol, polyethylene glycol and the like.

Lubricants can be chosen from, but not limited to, stearic acid, magnesium stearate, calcium stearate, aluminium stearate, sodium stearyl fumarate, talc, hydrogenated castor oil, polyethylene glycols and the like.

The active ingredients of the present invention can be formulated into the composition as neutralized pharmaceutically acceptable salt forms. Pharmaceutically acceptable salts include, but are not limited to, the acid addition salts, which are formed with inorganic acids such as, for example, hydrochloric, sulfuric or phosphoric acids, or such organic acids as acetic, oxalic, tartaric, mandelic, citric and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutical composition of the present invention may be formulated for sustained release. The release rate of the active agents is primarily controlled by dissolution of the active agents in gastrointestinal fluid and subsequent diffusion out of the tablet or capsule independent of pH, but can also be influenced by physical processes of disintegration and erosion of the tablet or capsule. Pharmaceutical compositions according to the invention achieve a therapeutic blood/plasma concentration of the anti-androgen agent and the antibiotic or anti-inflammatory agent in an individual for at least about 8 to about 14 hours from a single dose. The anti-androgen agent and antibiotic/anti-inflammatory agent may be released from the tablet or capsule to result in a therapeutic blood/plasma concentration for at about 8, 9, 10, 11, 12, 13 or 14 hours from a single dose.

The pharmaceutical composition may be an immediate release composition, i.e., a composition in which the whole quantity of the anti-androgen agent and/or the antibiotic/anti-inflammatory agent is released immediately after administration. Such immediate release compositions disperse readily to form a suspension or solution of the active agents after mixing with the saliva, which is easily swallowed by the patients. These are particularly suitable for children or aged patients who have difficulty in chewing and/or swallowing an intact tablet/capsule.

The anti-androgen agent and antibiotic/anti-inflammatory agent may be formulated as micronized or non-micronized particles. The non-micronized particles refer to particles having a particle size between 20-90 microns. The micronized particles refer to particles having a particle size between 1-20 microns. The particles may be formulated as solid or liquid dosage forms for oral administration.

The preparation of pharmaceutical compositions that contain an active component is well understood in the art, for example by mixing, granulating, or tablet-forming processes. The active agent is often mixed with excipients that are pharmaceutically acceptable and compatible with the active agent. For oral administration, the anti-androgen agent and/or the antibiotic or anti-inflammatory agent of this invention or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the compounds of this invention or their physiologically tolerated derivatives such as salts, esters, N-oxides, and the like are converted into a solution, suspension, or emulsion, if desired with the substances customary and suitable for this purpose, for example, solubilizers or other like agents.

One of ordinary skill in the art will appreciate that the individual components of the present invention may change depending on the physical and chemical qualities needed for the pharmaceutical compositions in a given process and/or application to which the pharmaceutical compositions will be applied.

Abbreviations and Definitions:

"Alkyl" is defined herein to mean, unless otherwise specified, a saturated straight, branched, or cyclic, primary, secondary, or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Alkyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, or any other viable functional group that does not inhibit the pharmacological activity of this compound, either unprotected, or protected, as necessary, as known to those skilled in the art, for example, as taught in T. W. Greene and P. G. M. Wuts, "Protective Groups in Organic Synthesis," 3rd ed., John Wiley & Sons, 1999, hereby incorporated by reference.

"Acyl" is defined herein to mean, unless otherwise specified, a carboxylic acid ester in which the non-carbonyl moiety of the ester group is selected from straight, branched, or cyclic alkyl, alkoxyalkyl including methoxymethyl, aralkyl including benzyl, aryloxyalkyl such as phenoxymethyl, aryl including phenyl optionally substituted with halogen (F, Cl, Br, I), $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group.

"Liposome" is defined herein to mean any enclosed vehicle made of a lipid bilayer which can be used to deliver active agents.

"Active agent" is defined herein to mean a compound given to a host to elicit a desired effect.

"Synergistic" is defined herein to mean the joint action of the drugs is such that the combined effect is greater than the algebraic sum of their individual parts.

"Pharmaceutical composition" is defined herein to mean a therapeutically effective amount of the anti-androgen agent and antibiotic/anti-inflammatory agent.

"Therapeutically effective amount" is defined herein to mean an amount which provides a therapeutic effect for a given condition and administration regimen.

"Pharmaceutically acceptable" is defined herein to mean any formulation which is safe, and provides the appropriate delivery for the desired route of administration of an effective amount of at least one compound for use in the present invention.

"Administering" is defined herein to mean bringing a subject in contact with the combination of the present invention.

"Sustained release" is defined herein to mean that the anti-androgen agent and antibiotic/anti-inflammatory agent becomes available for bio-absorption in the gastrointestinal tract over a prolonged period of time.

"Immediate release" is defined herein to mean a composition in which the whole quantity of the anti-androgen agent and antibiotic/anti-inflammatory agent is released immediately after administration.

"Therapeutic blood/plasma concentration" is defined herein to mean a concentration equal to at least about 50% of the AUC and/or $C_{max}$ of the anti-androgen agent and antibiotic/anti-inflammatory agent administered to a human subject.

The terms "suppressing", "inhibiting", "preventing", "alleviating" or "treating" are defined herein to mean delaying the onset of symptoms, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, preventing relapse to a disease, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics.

EXAMPLES

Example 1

Formulation

The preferred formulation for the disclosed composition (Formula 1) is doxycycline hyclate (50 mg; antibiotic) and S-equol (5 mg; isoflavandiol). One skilled in the art will recognize that alternative equivalent formulations are encompassed by this example.

Example 2

Formula 1 reduces comedones and inflammatory lesions and improves acne in patients.

Thirty-five patients (13-55 years of age) were enrolled in a placebo-controlled study. Twenty-seven patients were treated with oral administration of a capsule containing the ingredients of Formula 1 and eight patients were treated with a placebo capsule containing only doxycycline hyclate (50 mg). Patients received Formula 1 or placebo twice daily for twelve weeks. The number of comedones ("blackheads") and nodular and inflammatory lesions (>2 mm in diameter) were counted on the face of each patient at baseline and at two weeks, six weeks and twelve weeks post-treatment. No serious untoward effects were observed in either the treated or placebo groups.

Formula 1 significantly reduced the number of comedones and nodular and inflammatory lesions during the twelve week treatment cycle (Table 1). The results are shown as the change at baseline and the percent change from baseline for each outcome measure after twelve weeks of treatment. Data are reported as mean values (±standard error of the mean, SEM) for each outcome measure. The results for 'total lesions' includes both comedones and inflammatory and nodular lesions.

TABLE 1

Summary Lesion Counts at 12-weeks[1]

| Parameter | Treated Group (n = 27) Avg (SEM) | Placebo Group (n = 8) Avg (SEM) |
|---|---|---|
| Total Inflammatory and Nodular Lesions | | |
| Baseline | 20.8(1.9) | 14.3(2.8) |
| 12-weeks | 7.2(2.2) | 7.0(3.4) |
| Change from baseline | −20.2(3.6) | −7.0(6.8) |
| Change from baseline, % | −65.5% | −50.9% |
| Total Comedones | | |
| Baseline | 33.3(2.9) | 26.9(8.1) |
| 12-weeks | 19.3(4.3) | 19.5(7.2) |
| Change from baseline | −18.3(6.3) | −7.3(9.1) |
| Change from baseline, % | −42.0% | −27.4% |
| Total Lesions | | |
| Baseline | 54.1(4.4) | 41.1(9.3) |
| 12-weeks | 26.5(6.2) | 26.5(4.1) |
| Change from baseline | −36.8(10.3) | −14.3(15.2) |
| Change from baseline, % | −51.0% | −35.6% |

[1]Unless otherwise indicated, data are mean (SE) number of lesions

The average number of comedones continued to decline with treatment compared to inconsistent observations of the placebo group. For example, Formula 1 treatment significantly reduced the number of comedones in the treated group from 33.3 (±2.9) at baseline to 19.3 (±4.3; p=0.03) at 12 weeks while a more varied response was observed for the placebo group (26.9, 29.0, 11.8 and 19.5 at baseline, week 2, week 6 and week 12, respectively). Thus, Formula 1 reduced the average number of comedones by 42% at twelve weeks compared to baseline in the treatment group to 27.4% reduction in the placebo group. Formula 1 was also 15% more effective in reducing the total number of lesions (including comedones and inflammatory and nodular lesions) in the treatment group (51.0%) compared to the placebo group (35.6%) after twelve weeks of treatment.

Next, an Investigator Global Assessment (IGA) score measuring the improvement of the appearance of inflammatory and nodular lesions and comedones was determined for each patient at baseline and 2 weeks and 6 weeks post-treatment. For this assessment the investigators were asked to evaluate whether their patient's lesions and comedones improved using a score of 1 to 10 with 10 indicating the most improvement. Treatment with Formula 1 improved the IGA scores in the treated patients from 2.5 at baseline to 4.0 at six weeks while the IGA scores in the placebo group did not change (2.3 at baseline to 2.5 at six weeks).

Lastly, the Visia™ complexion analysis system was used to assess the average number of porphyrins, a measure of bacteria in pores, in each patient. Treatment with Formula 1 reduced the average number of porphyrins in the treatment group while a slight increase in porphyrins was observed in the placebo group (Table 2).

TABLE 2

|  | Por (BL) | Por (W2) | Por (W6) | Por (W12) |
|---|---|---|---|---|
| Average (Drug) | 50.6 | 46.4 | 20.4 | 15.5 |
| Average (Placebo) | 31.6 | 25.8 | 15.7 | 35.5 |
| SEM (Drug) | 13.6 | 11.9 | 5.5 | 3.7 |
| SEM (Placebo) | 15.7 | 8.7 | 5.5 | 18.0 |

In summary, this example shows that Formula 1 significantly reduced the number of comedones, inflammatory and nodular lesions by 15% compared to baseline in the treatment group as well markedly reducing the number of porphyrins during the course of the study.

All patents, patent applications and publications cited in this application are hereby incorporated by reference in their entirety for all purposes to the same extent as if each individual patent, patent application or publication were so individually denoted.

Although certain embodiments and examples have been described in detail above, those having ordinary skill in the art will clearly understand that many modifications are possible in the embodiments and examples without departing from the teachings thereof. All such modifications are intended to be encompassed within the below claims of the invention.

This application claims benefit of U.S. Provisional Patent Application Ser. Nos. 61/349,240 filed May 28, 2010 and 61/369,391 filed Jul. 30, 2010.

What is claimed is:

1. A pharmaceutical composition comprising 4',7-isoflavandiol or a pharmaceutically acceptable salt or hydrate thereof; doxycycline or a pharmaceutically acceptable salt or hydrate thereof; and a pharmaceutically acceptable excipient, wherein the composition is in a unit dosage form comprising 5-10 mg of 4',7-isoflavandiol or a pharmaceutically acceptable salt or hydrate thereof and 50-100 mg of doxycycline or a pharmaceutically acceptable salt or hydrate thereof.

2. The pharmaceutical composition of claim 1, wherein the salt or hydrate of doxycycline is doxycycline monohydrate or doxycycline hyclate.

3. The pharmaceutical composition of claim 1, wherein the 4',7-isoflavandiol or the pharmaceutically acceptable salt or hydrate thereof is present in a racemic mixture.

4. The pharmaceutical composition of claim 1, wherein the 4',7-isoflavandiol or the pharmaceutically acceptable salt or hydrate thereof is present in the "S-" form.

5. The pharmaceutical composition of claim 1, wherein the composition further comprises an oral contraceptive, an estrogen analog, a progesterone analog, inocoterone acetate, cyproterone acetate, flutamide, nilutamide, bicalutamide, keto-conazole, finasteride, dutasteride, bexlosteride, izonsteride, epresteride, turosteride, isoflavanoid, RU-58642, RU-56279, WS9761 A and B, RU-59063, RU-58841, bexlosteride, LG-2293, L-245976, LG-121071, LG-121091, LG-121104, LGD-2226, LGD-2941, YM-92088, YM-175735, LGD-1331, LGD-3303, BMS-357597, S-40503, BMS-482404, EM-4283, EM-4977, BMS-564929, BMS-391197, BMS-434588, BMS-487745, BMS-501949, SA-766, YM-92088, YM-580, LG-123303, LG-123129, PMCo1, YM-175735, BMS-591305, BMS-591309, BMS-665139, BMS-665539, CE 590, 116BG33, 154BG31, arcarine, ACP-105, flutamide, hydroxyflutamide, bicalutamide, nilutarnide, a hydroxy-steroid dehydrogenase inhibitor, a PPARα ligand, a dual acting PPAR ligand, PN-2034, PPAR δ, a 17-ketoreductase inhibitor, a 3β-DHΔ4,6-isomerase inhibitor, a 3β-DHΔ4,5-isomerase inhibitor, a 17,20 desmolase inhibitor, a p450c17 inhibitor, a p450ssc inhibitor, or a 17,20-lyase inhibitor.

6. The pharmaceutical composition of claim 1, wherein the composition is formulated for oral administration.

7. The pharmaceutical composition of claim 6, wherein the composition is formulated as a solid or liquid dosage form.

8. The pharmaceutical composition of claim 7, wherein the solid dosage form is a tablet, capsule, or pill or comprises granules, pellets or powders.

9. The pharmaceutical composition of claim 7, wherein the liquid dosage form is a solution, suspension, dispersion, emulsion, foam, gel, or oil.

10. The pharmaceutical composition of claim 1, wherein the composition is formulated for topical administration.

11. The pharmaceutical composition of claim 10, wherein the composition comprises liposomal beads or is formulated as a gel, ointment, cream, or lotion.

12. The pharmaceutical composition of claim 10, wherein the composition is formulated as a transdermal patch.

* * * * *